US009945854B2

(12) United States Patent
Altman et al.

(10) Patent No.: US 9,945,854 B2
(45) Date of Patent: Apr. 17, 2018

(54) METHODS OF MEASURING POTENTIAL FOR THERAPEUTIC POTENCY AND DEFINING DOSAGES FOR AUTOLOGOUS CELL THERAPIES

(71) Applicant: BioCardia, Inc., San Carlos, CA (US)

(72) Inventors: Peter Altman, Menlo Park, CA (US); Cheryl Wong Po Foo, Santa Clara, CA (US)

(73) Assignee: BioCardia Inc., San Carlos, CA (US)

( * ) Notice: Subject to any disclaimer, the term of this patent is extended or adjusted under 35 U.S.C. 154(b) by 0 days.

(21) Appl. No.: 15/693,679

(22) Filed: Sep. 1, 2017

(65) Prior Publication Data

US 2017/0363623 A1 Dec. 21, 2017

Related U.S. Application Data

(63) Continuation of application No. 14/526,222, filed on Oct. 28, 2014, now abandoned.

(60) Provisional application No. 61/896,450, filed on Oct. 28, 2013.

(51) Int. Cl.
*G01N 33/53* (2006.01)
*G01N 33/569* (2006.01)
*A61K 35/28* (2015.01)

(52) U.S. Cl.
CPC ....... *G01N 33/56966* (2013.01); *A61K 35/28* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,097,832 | B1 | 8/2006 | Kornowski et al. |
| 7,695,712 | B2 | 4/2010 | Poznansky et al. |
| 8,496,926 | B2 | 7/2013 | De La Fuente et al. |
| 2006/0034290 | A1 | 2/2006 | Kalofonos et al. |
| 2006/0040392 | A1 | 2/2006 | Collins et al. |
| 2007/0148668 | A1 | 6/2007 | Rich |
| 2007/0249047 | A1 | 10/2007 | McKenna, Jr. et al. |
| 2010/0127342 | A1 | 5/2010 | Mabuchi |
| 2012/0208275 | A1* | 8/2012 | Walton .................. C12N 5/0647 435/373 |
| 2015/0118199 | A1 | 4/2015 | Altman et al. |

FOREIGN PATENT DOCUMENTS

| | | |
|---|---|---|
| WO | WO-2006060591 A2 | 6/2006 |
| WO | WO-2009146495 A1 | 12/2009 |
| WO | WO-2015066076 A1 | 5/2015 |

OTHER PUBLICATIONS

Beksac, et al. Is it time to revisit our current hematopoietic progenitor cell quantification methods in the clinic? Bone marrow transplantation 47.11 (2012): 1391-1396.
De La Fuente, et al. Transendocardial autologous bone marrow in myocardial infarction induced heart failure, two-year follow-up in an open-label phase I safety study (The TABMMI study). EuroIntervention. Nov. 2011;7(7):805-12. doi: 10.4244/EIJV717A127.
Deng, et al. Noninvasive discrimination of rejection in cardiac allograft recipients using gene expression profiling. Am J Transplant. 6(1):150-60, 2006.
European search report and search opinion dated Apr. 25, 2017 for EP Application No. 14857113.6.
Goodchild, et al. Bone marrow-derived B cells preserve ventricular function after acute myocardial infarction. J Am Coll Cardiol Intv 2009; 2:1005-16.
Human Cell Differentiation Molecules: CD nomeclature and list. Accessed Nov. 7, 2014. http://www.uniprot.org/docs/cdlist.
Human Cell Differentiation Molecules (HCDM) website. Accessed Nov. 7, 2014. Http://www.hcdm.org.
International search report and written opinion dated Feb. 23, 2015 for PCT/US2014/062724.
Kara, et al. Flow cytometric evaluation of bone marrow plasma cells using CD19, CD45, CD56, CD38, and CD138 and correlation with bone marrow infiltration ratio in multiple myeloma patients. Saudi Med J. Nov. 2004;25(11):1587-92.
Loken, et al. Flow cytometric analysis of human bone marrow. II. Normal B lymphocyte development. Blood. Nov. 1987;70(5):1316-24.
Losordo, et al. Intramyocardial, autologous CD34+ cell therapy for refractory angina. Circ Res. Aug. 5, 2011;109(4):428-36. doi: 10.1161/CIRCRESAHA.111.245993. Epub Jul. 7, 2011.
Office action dated Jan. 20, 2016 for U.S. Appl. No. 14/526,222.
Office action dated Aug. 2, 2016 for U.S. Appl. No. 14/526,222.
Perin, et al. A randomized study of transendocardial injection of autologous bone marrow mononuclear cells and cell function analysis in ischemic heart failure (FOCUS-HF). Am Heart J. Jun. 2011;161(6):1078-87.e3. doi: 10.1016/j.ahj.2011.01.028. Epub May 10, 2011.
Perin, et al. Effect of transendocardial delivery of autologous bone marrow mononuclear cells on functional capacity, left ventricular function, and perfusion in chronic heart failure: the FOCUS-CCTRN trial. JAMA. Apr. 25, 2012;307(16):1717-26. doi: 10.1001/jama.2012.418. Epub Mar. 24, 2012.
Taylor, et al. Improved Myocardial Function in Patients with Chronic Ischemic Heart Disease Treated with Transendocardial Delivery of Bone Marrow Mononuclear Cells Depends Upon Input Cell Phenotype and Function. (2012): A16354-A16354.

(Continued)

*Primary Examiner* — Changhwa J Cheu
(74) *Attorney, Agent, or Firm* — Wilson, Sonsini, Goodrich & Rosati

(57) ABSTRACT

Autologous bone marrow cells (BMC) are transplanted to a heterologous site in a patient after a sample of the patient's BMC has been tested and found to have a phenotypic profile which meets minimum criteria for transplantation. The phenotypic profile may be obtained by screening a sample of bone marrow cells (BMC) from the patient for the phenotypic profile, such as a CD profile, the phenotype profile may be assessed to determine the likelihood that the BMC will be suitable for transplantation to the heterologous tissue site without enriching particular phenotypic population(s) of the BMC.

7 Claims, 10 Drawing Sheets

(56) References Cited

OTHER PUBLICATIONS

Warshawsky, et al. Engraftment Analysis Using Short Tandem Repeats Following Allogeneic Hematopoietic Cell Transplanation,: Laboratory Hematology Practice, Aug. 8, 2012 (Aug. 8, 2012), Chapter 19, p. 236. entire document.

European Examination Report dated Nov. 8, 2017 for EP Patent Application No. 14857113.6.

Keeney, et al. "Hematopoietic Stem Cells: Issues in Enumeration In: Applications of Flow Cytometry in Stem Cell Research and Tissue Regeneration", Jul. 28, 2010, John Wiley & Sons, Inc., Hoboken, NJ, USA, pp. 115-134.

\* cited by examiner

Figure 2

| Reported Studies | Total Dose | Percent | | | Cell Count- Calculated (Total Dose x Percent) | | | Percent Retention | Estimated Cells Retained-Calculated (Cell Count x Percent Retention) | | |
|---|---|---|---|---|---|---|---|---|---|---|---|
| | | CD34 | CD133 | CD19 | CD34 | CD133 | CD19 | | CD34-R | CD133-R | CD19-R |
| ACT34-CMI 2011 | 7000000 | 100.00% | | | 7000000 | 0 | 0 | 6.00% | 420000 | 0 | 0 |
| TABMMI 2011 | 100000000 | 1.90% | 0.20% | 2.4%* | 1900000 | 200000 | 2400000* | 18.00% | 342000 | 36000 | 432000* |
| FOCUS-HF 2011 | 30000000 | 1.50% | 0.2%* | 2.40% | 450000 | 60000* | 720000 | 6.00% | 27000 | 3600* | 43200 |
| FOCUS-CCTRN 2012 | 100000000 | 2.71% | 1.21% | 2.4%* | 2710000 | 1210000 | 2400000* | 6.00% | 162600 | 72600 | 144000* |

*Extrapolated from TABMMI 2011
¥Extrapolated from FOCUS-HF 2011

Figure 4

| Reported Studies | Total Dose | Percent CD34 | CD133 | CD19 | Cell Count- Calculated (Total Dose x Percent) CD34 | CD133 | CD19 | Percent Retention | Estimated Cells Retained-Calculated (Cell Count x Percent Retention) CD34-R | CD133-R | CD19-R |
|---|---|---|---|---|---|---|---|---|---|---|---|
| ACT34-CMI 2011 | 7000000 | 100.00% | | | 7000000 | 0 | 0 | 6.00% | 420000 | 0 | 0 |
| TABMMI 2011 | 100000000 | 1.90% | 0.20% | 2.4%¥ | 1900000 | 200000 | 2400000¥ | 18.00% | 342000 | 36000 | 432000¥ |
| FOCUS-HF 2011 | 30000000 | 1.50% | 0.2%* | 2.40% | 450000 | 60000* | 720000 | 6.00% | 27000 | 3600* | 43200 |
| FOCUS-CCTRN 2012 | 100000000 | 2.71% | 1.21% | 2.4%¥ | 2710000 | 1210000 | 2400000¥ | 6.00% | 162600 | 72600 | 144000¥ |
| Effective minimum dosage needed to be achieved with the Helix | | | | | | | | | 420000 | 72600 | 144000 |
| Minimum cells per cc of marrow aspirate (Effective minumum dosage / (percent retention x 60 ml bone marrow aspirate) | | | | | | | | | 38889 | 6722 | 13333 |

*Extrapolated from TABMMI 2011
¥Extrapolated from FOCUS-HF 2011

Figure 5

| Reported Studies | Total Dose | Percent CD34 | CD133 | CD19 | Cell Count- Calculated (Total Dose x Percent) CD34 | CD133 | CD19 | Percent Retention | Estimated Cells Retained-Calculated (Cell Count x Percent Retention) CD34-R | CD133-R | CD19-R |
|---|---|---|---|---|---|---|---|---|---|---|---|
| ACT34-CMI 2011 | 7000000 | 100.00% | | | 7000000 | 0 | 0 | 6.00% | 420000 | 0 | 0 |
| TABMMI 2011 | 100000000 | 1.90% | 0.20% | 2.4%* | 1900000 | 200000 | 2400000* | 18.00% | 342000 | 36000 | 432000¥ |
| FOCUS-HF 2011 | 30000000 | 1.50% | 0.2%* | 2.40% | 450000 | 60000* | 720000 | 6.00% | 27000 | 3600* | 43200 |
| FOCUS-CCTRN 2012 | 100000000 | 2.71% | 1.21% | 2.4%* | 2710000 | 1210000 | 2400000* | 6.00% | 162600 | 72600 | 144000¥ |
| Effective minimum dosage needed to be achieved with the Helix | | | | | | | | | 162600 | 72600 | 144000 |
| Minimum cells per cc of marrow aspirate (Effective minumum dosage / (percent retention x 60 ml bone marrow aspirate) | | | | | | | | | 15056 | 6722 | 13333 |

*Extrapolated from TABMMI 2011
¥Extrapolated from FOCUS-HF 2011

Figure 6

| Reported Studies | Total Dose | Percent | | | Cell Count- Calculated (Total Dose x Percent) | | | | Percent Retention | Estimated Cells Retained-Calculated (Cell Count x Percent Retention) | | |
|---|---|---|---|---|---|---|---|---|---|---|---|---|
| | | CD34 | CD133 | CD19 | CD34 | CD133 | CD19 | | | CD34-R | CD133-R | CD19-R |
| ACT34-CMI 2011 | 7000000 | 100.00% | | | 7000000 | 0 | 0 | | 6.00% | 420000 | 0 | 0 |
| TABMMI 2011 | 100000000 | 1.90% | 0.20% | 2.4%* | 1900000 | 200000 | 2400000* | | 18.00% | 342000 | 36000 | 432000* |
| FOCUS-HF 2011 | 30000000 | 1.50% | 0.2%* | 2.40% | 450000 | 60000* | 720000 | | 6.00% | 27000 | 3600* | 43200 |
| FOCUS-CCTRN 2012 | 100000000 | 2.71% | 1.21% | 2.4%* | 2710000 | 1210000 | 2400000* | | 6.00% | 162600 | 72600 | 144000* |

Effective minimum dosage needed to be achieved with the Helix | | | | | | | | | | 162600 | 72600 | 144000

Assuming 20% cell loss during point of care cell processing
Minimum cells per cc of marrow aspirate (((Effective minimum dosage / (percent retention x 54 ml bone marrow aspirate))/0.8) | | | | | | | | | | 20910 | 9336 | 18519

Assuming 50% cell loss during point of care cell processing
Minimum cells per cc of marrow aspirate (((Effective minimum dosage / (percent retention x 54 ml bone marrow aspirate))/0.5) | | | | | | | | | | 33457 | 14938 | 29630

*Extrapolated from TABMMI 2011
¥Extrapolated from FOCUS-HF 2011

Figure 8

Estimated Cells Retained @ One Hour (from a 60 cc bone marrow aspirate (BMA))

| CD34 (Losordo 2011) | CD133 (FOCUS-CCTRN 2012) | CD19 (FOCUS-CCTRN 2012, extrapolated from FOCUS-HF 2011) |
|---|---|---|
| 420000 | 72600 | 144000 |

These calculated cell dosages are the effective dosages. The estimated cell count required from 1 or 10 cc of BMA below are based on the assumption that for the effective dosages, cells are 100% retained @ one hour starting from a 60 cc BMA.

Calculated Effective Dosage from 1 cc BMA

| CD34 | CD133 | CD19 |
|---|---|---|
| 7000 | 1210 | 2400 |

Calculated Effective Dosage from 10 cc BMA

| CD34 | CD133 | CD19 |
|---|---|---|
| 70000 | 12100 | 24000 |

Helical Infusion System -- 18 % of cells delivered are assumed to be retained @ one hour Estimated Cell Count Required from 1 cc BMA

| CD34 | CD133 | CD19 |
|---|---|---|
| 38889 | 6722 | 13333 |

Estimated Cell Count Required from 10 cc BMA

| CD34 | CD133 | CD19 |
|---|---|---|
| 388889 | 67222 | 133333 |

Straight Needle System -- 6% of cells delivered are assumed to be retained @ one hour Estimated Cell Count Required from 1 cc BMA

| CD34 | CD133 | CD19 |
|---|---|---|
| 116667 | 20167 | 40000 |

Estimated Cell Count Required from 10 cc BMA

| CD34 | CD133 | CD19 |
|---|---|---|
| 1166667 | 201667 | 400000 |

Intracoronary Delivery -- 1% of cells infused are assumed to be retained @ one hour Estimated Cell Count Required from 1 cc BMA

| CD34 | CD133 | CD19 |
|---|---|---|
| 700000 | 121000 | 240000 |

Estimated Cell Count Required from 10 cc BMA

| CD34 | CD133 | CD19 |
|---|---|---|
| 7000000 | 1210000 | 2400000 |

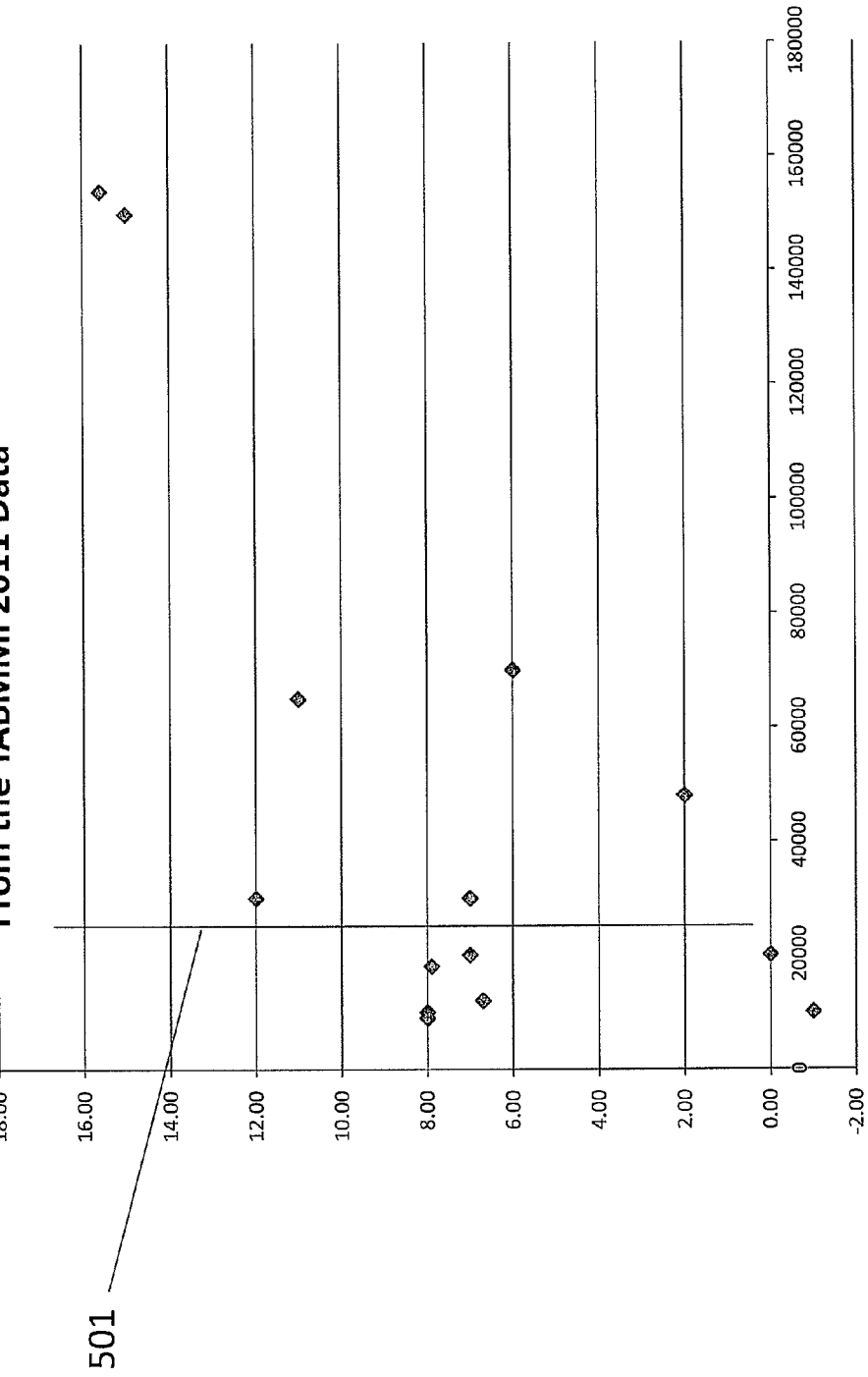
Figure 9. Improvements in EF Versus CD133 Cells Delivered with Helix From the TABMMI-2011 Data

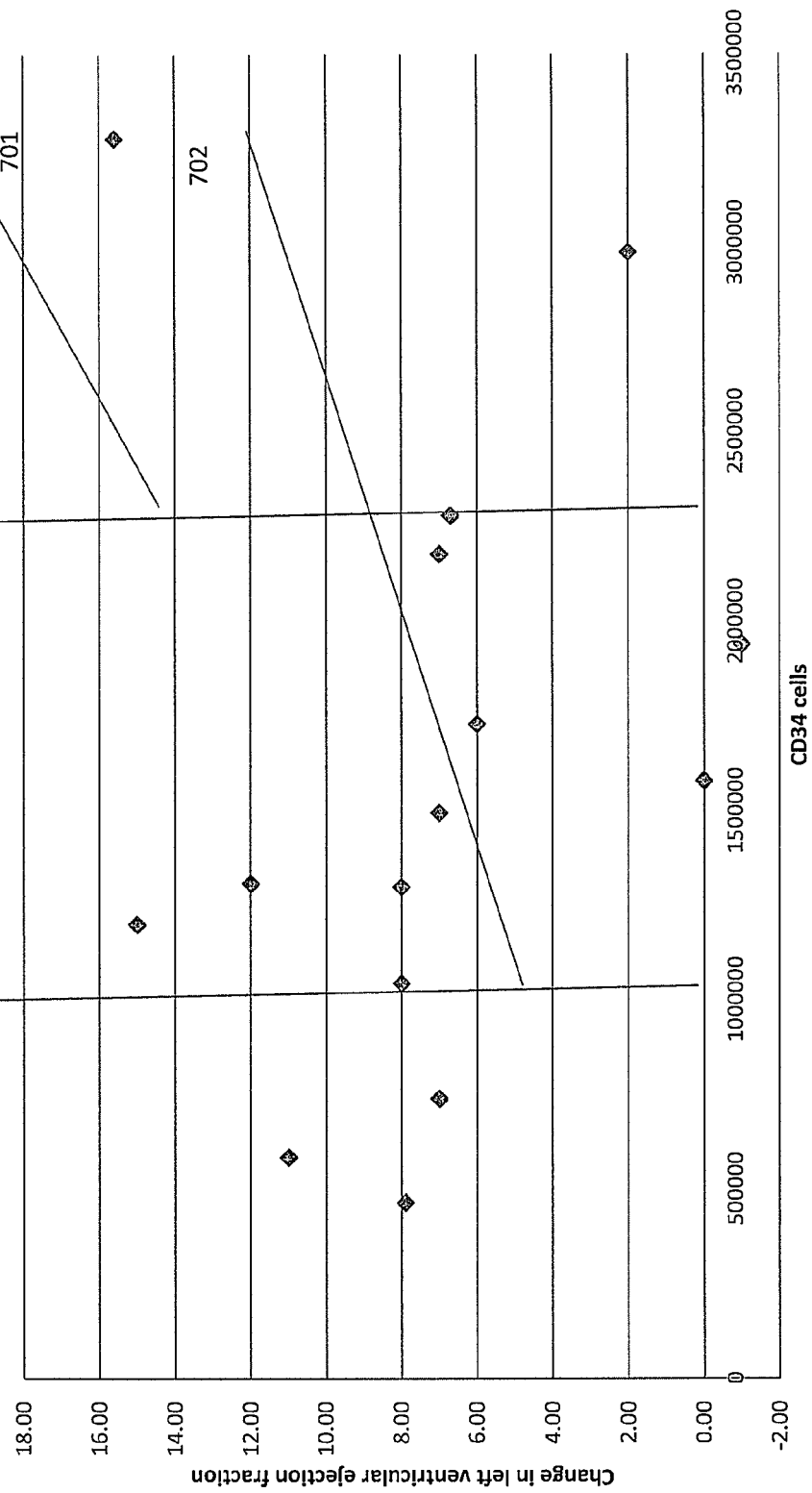

METHODS OF MEASURING POTENTIAL FOR THERAPEUTIC POTENCY AND DEFINING DOSAGES FOR AUTOLOGOUS CELL THERAPIES

CROSS-REFERENCE TO RELATED APPLICATIONS

This application is a continuation of application Ser. No. 14/526,222, filed on Oct. 28, 2014, which claimed the benefit of Provisional Application No. 61/896,450, filed Oct. 28, 2013, the full disclosures of which are incorporated herein by reference.

BACKGROUND OF THE INVENTION

Introduction to Pharmacogenomics and Personalized Medicine. Pharmacogenomics is the field of selecting the right drug for the right patient at the right time. Its genesis was the belief that the pharmaceutical industry would identify and match patients with specific genetic phenotypes and gene expression profiles who would respond to specific therapeutic medicines, providing a new era of personalized medicine. This would inherently enhance the drugs therapeutic profile, resulting in more successful clinical trial results as the selected patients would have already been identified as potential responders to the therapy. An example of a successful drug that has been developed using the concept of pharmacogenomics is the drug Herceptin. It is currently used in the treatment of early stage Human Epidermal growth factor Receptor-2 (HER-2) positive and late stage HER-2 positive metastatic breast cancer where an overexpression of the protein marker HER-2 is caused by a gene mutation in the cancerous cell. This genetic mutation is present in one out of every five breast cancers. Herceptin specifically targets HER-2 to kill the cancer cells and is often used with chemotherapy to decrease the risk of cancer recurrence. Therefore, patient testing HER-2 positive is a pre-specified requirement for treatment with Herceptin.

The concept of selecting patients who are predisposed to respond to particular therapies has tremendous potential. A number of efforts have been put forth in the development of gene expression assays to characterize cancer tumors based on their gene activity—i.e., up regulation or down regulation of specific genetic markers or a genetic mutation specific to the type of cancerous cells. These gene expression assays would allow a more accurate understanding of the cause of the disease from a genetic standpoint which would result in the ability to pinpoint the specific pathway via which these genes are getting up or down regulated or mutated. Therefore, a patient's responsiveness to expensive and often dangerous chemotherapy that is not specifically tailored to the patient's individual needs, could be evaluated in advance of the therapy which would reduce cost but above all, would prevent the patient from going through unnecessary painful treatments. Genomic Health's OncotypeDx gene expression assay is an example of such a product which is generating millions of dollars per year as a diagnostic assay to determine whether or not a patient has a high likelihood of responding to therapy. Other new products on the market, CareDx's Allomap assay and CardioDx's Corus test are designed to determine whether or not a patient should be subjected to a more invasive assay to assess the status of the disease. For CareDx's Allomap assay, gene expression analysis of the circulating white cells in the blood is intended to determine if the patient's circulating immune system is calm or angry. If calm, the patient does not need to have an invasive heart biopsy and may even have their dosage of potentially dangerous immunosuppressant drugs lowered. If angry, the patient needs to have a biopsy, which, if positive, is likely to result in an increased immunosuppression regimen. For the CardioDx Corus test, the blood based leukocyte gene expression signature is used to safely and quickly help identify whether a patient presenting with chest pain is likely suffering from obstructive coronary artery disease and would require a coronary angiogram to look for a diseased artery or a heart attack. These are merely three examples of a new field of endeavor in which patient specific information is used to help determine appropriate next steps for informed patient care management. This may and oftentimes does include significant and expensive clinical care decisions, and these tests therefore have value in both mitigating the risks of unnecessary and potentially dangerous procedures and reducing medical costs.

Introduction to Autologous Tissue Therapies. In medicine, there are many autologous therapies in which a tissue or material is extracted from a patient and is returned to the patient for therapeutic purposes. Autologous therapies can be classified as homologous and non-homologous. Homologous autologous therapies constitute harvesting a tissue from one part of the body and using it to serve the same basic function whether it is in the same or a different part of the body of a patient. Examples of homologous autologous therapies include the harvest of skin from a less visible part of the body to perform a graft on the face of a burn victim; the use of bone from one part of the body to help reconstruct another more important and critical bone structure; and the extraction of cartilage from one part of the body and its ex vivo culture and expansion for re-implantation into the body later. Non-homologous therapies are those in which the harvested tissue and preparations thereof either by concentration, selection, expansion, modification by adding ligands, culture or any combinations of these are intended to serve a different purpose than the tissues were serving at their time of harvest. This does not mean they may not mimic natural processes, but rather that they were harvested and are being repurposed from their status at time of harvest. Non-homologous cell therapies include the delivery of cells or tissues to treat cardiovascular disease, autoimmune diseases, diabetes, metabolic disorders, and a broad variety of cancers.

Cardiovascular indications include acute myocardial infarction, chronic myocardial ischemia, heart failure of ischemic etiology (with active ischemia or chronically infarcted without the presence of active ischemia) or non-ischemic etiology, or cardiac arrhythmias, refractory angina, dilated cardiomyopathy. U.S. Pat. No. 7,097,832 issued to Kornowski and U.S. Pat. No. 8,496,926 issued to de la Fuente describe such therapeutic strategies to treat cardiovascular disease using bone marrow derived cells. Autologous non-homologous tissues that have been investigated preclinically and clinically for such non-homologous cardiac therapeutic purposes are extensive and include bone marrow cells, bone marrow or peripheral blood mononuclear cells, bone marrow or blood derived CD34 cells (whether harvested from the bone marrow or from the blood after GCSF stimulated release), bone marrow or blood derived CD133 cells; bone marrow or blood derived CD 19 cells, bone marrow or blood derived ALDH bright positive cells, bone marrow derived and ex vivo expanded mesenchymal cells, bone marrow derived and expanded mesenchymal precursor or progenitor cells, adipose tissue derived cells, and umbilical cord derived cells. Other non-homologous tissues that have been used preclinically include c-kit+ cells, placental-derived cells, human amniotic mesenchymal stem cells. Many of these autologous therapies have been indicated for the treatment of other diseases such as chronic limb ischemia and intermittent claudication as well as autoimmune and inflammatory diseases such as inflammatory bowel diseases of ulcerative colitis, Crohn's disease, lupus, osteoarthritis, diabetes and kidney diseases.

The use of activated T-cells, tumor infiltrating leukocytes, and activated dendridic cells have an expanding role in immunotherapy today and often involve removing dendritic cells or t cells from the patient and modifying them to enable them to more accurately and aggressively attack tumor cells when they are re-administered to the patient. Dendritic cells are antigen-presenting cells, (also known as accessory cells) of the mammalian immune system. Their main function is to process antigen material and present it on the cell surface to the T cells of the immune system. Dendritic cells act as messengers between the innate and the adaptive immune systems. T cells or T lymphocytes are a type of lymphocyte (a type of white blood cell) that play a central role in cell-mediated immunity. They can be distinguished from other lymphocytes, such as B cells and natural killer cells (NK cells), by the presence of a T-cell receptor (TCR.,) on the cell surface. They are called T cells because they mature in the thymus (although some also mature in the tonsils). There are several subsets of T cells, each with a distinct function.

Tissue based autologous therapies, by their nature are personalized and depend on a number of variables including the patient's age, sex, race, weight, extent of cardiovascular disease progression and the presence of comorbidities such as diabetes, hypertension, angina, hyperlipidemia among others. All patients do not have the same cells in the same concentrations with the same genes or gene expression profiles. All patients do not have the same therapeutic potential in their tissues for a given clinical indication nor will all patients respond to a therapy identically even if the therapeutic potential of a given dosage form is identical. This is a critical problem in the field.

Different approaches have been used to try and solve various aspects of this problem, with particular focus on cardiovascular disease, the leading cause of death in the western world. One potential solution is to attempt to make autologous cell therapy as close to a pure pharmaceutical preparation as possible. Examples of such autologous cell therapy products for just cardiovascular applications include Baxter's or Neostem's selected CD34 cells in chronic myocardial ischemia and acute myocardial infarction, respectively; CellProThera's culture expanded CD34+ cells; Miltenyi's selected CD133 cells), culture-expanded Mesenchymal Stem Cells (MSCs), Dental Pulp Stem Cells (DPSCs), Cardio3 Biosciences culture expanded MSCs with ex vivo stimulated differentiation, Capricor's culture expended cardiosphere derived cells, autologous culture expanded CD271 positive cells, and expanded Hematopoietic Stem Cells (HSCs), and the like. Such autologous cell therapy products require extensive manipulation and analysis of the cells intended for treatment before they are returned to the patient to enable dosage formulations which are as standardized as possible. The cell manipulation often requires isolating cells with specific cell surface markers such as CD34 or CD133 from bone marrow or peripheral blood using antibodies bound to magnetic beads or other standard purification methods and expanding those isolated cell populations in culture outside of the patient's body to reach the desired dosage formulation required for treatment. That dosage could be determined based on patient weight or could be a same standardized dosage in terms of total number of cells to be delivered. Cell analysis usually includes performing functional assays such as mitogenic or colony forming unit assays (CFU-F, CFU-EC, CFU-HILL, etc.) on these cells to determine the cells' health and their proliferative potential. These types of extensive manipulation, cell culture handling and analysis significantly raise the costs of these proposed therapeutic candidates. Not only do the manipulations themselves have significant labor and complex reagents and materials costs, but they also have shipping and quality control costs on each patient's tissues, resulting in a separate manufacturing lot for each and every dosage form for one particular patient. Each assay on a potential autologous therapeutic dosage formulation and each step in its handling add significantly to the costs of the therapy—which in turn means that the developer and manufacturer will ultimately have to charge a higher price for their product. This approach however only addresses one issue by attempting to normalize the dosage in every patient but still does not result in identical dosages for these patients as we can only suggest that the cells performed similarly in the functional assays involved and passed the lot release testing specified by the developer for purity,functional assay, sterility and lack of contamination by infectious agents. This does not mean that the cells would behave the same way when re-injected in the patient. One example of an autologous cell therapy product for cardiovascular application that employed this selected cell strategy with a successful clinical trial outcome lies in Baxter's CD34 autologous cell therapy. The double-blind, prospective, randomized, placebo-controlled Phase II trial was designed to determine the tolerability, efficacy, safety, and dose range of intramyocardial injections of G-CSF mobilized autologous CD34 cells for a reduction of angina episodes in patients with refractory chronic myocardial ischemia (ACT34-CMI). The results of this trial published in Losordo D W et al. 2011 [Circ Res. 109: Intramyocardial, Autologous CD34+Cell Therapy for Refractory Angina] have shown that percutaneous intramyocardial injections of mobilized autologous peripheral blood derived CD34+ cells at dosages of $10^5$ cells/kg led to significant improvements in angina frequency and exercise tolerance.

Other purified cells with specific cell surface markers isolated from the bone marrow, include the CD19 bone marrow derived cells which have been shown to have potential efficacy that is superior to that of whole bone marrow or other cell subtypes in preclinical studies (Goodchild T et al. 2009, J Am Coll Cardiol Intv. 2: 1005-16). These cells are described in U.S. Pat. No. 7,695,712.

A second approach to the problem is to increase the uniformity of therapeutic cells delivered to each patient and eliminate the costs of analyzing the cells and of manufacturing a separate lot for each dosage formulation through the development of allogeneic tissue dosage formulations so that the tissue from one donor can be applied to thousands of patients. This strategy was previously in development by Osiris Therapeutics with Mesenchymal Stem Cells, and is currently being developed by Mesoblast with Mesenchymal Precursor Cells. Mesenchymal stem cells (or precursor cells or progenitor cells) have long been argued to be immune privileged cells such that the allogeneic donor cells will not be attacked by the circulating immune system of the recipient, thus making the possibility of a universal donor a realistic and extremely attractive one. In addition to being obviously more cost effective and commercially viable, this strategy, also has the advantage of enabling the selection of healthy young donors whose healthy cells have been shown to be much more efficacious that the older diseased patients' cells. Other groups including Capricor Therapeutics, Inc., a clinical stage biotechnology company that has migrated to developing allogeneic cardiac stem cells (CSC) after reporting results from autologous cells, has postulated that their allogenic CSC are not immune privileged as the allogeneic mesenchymal stem cells. The Capricor allogenic CSC are rejected or eliminated from the heart, but the cells are reported to have their therapeutic benefit before being rejected by the immune system of the recipient or otherwise eliminated. The problem with this therapeutic approach even if the theoretical assertions on the immune privilege status of mesenchymal stem cells or time course of action preceding rejection for CSCs hold true, is that each lot of cells will come from a different universal donor or a combination of donors and they will not be identical. Therefore, to a lesser extent, as in the first approach above, one should expect variations in response and in beneficial outcomes with each donor or batch lot and at present, one cannot presume these variations to be insignificant or predictable.

These current approaches for specific strategies for cell therapies are based on the classical pharmaceutical mindset of purification to optimize a dosage form that is the same for all patients, even if it is an autologous therapy. While this has value for advancing the status of our scientific knowledge and adds significant rigor to cell based therapies, it also adds enormously to the complexity of therapies when simpler approaches described herein are possible. Both of these approaches are intended to overcome what is seen as limitations with respect to the delivery of minimally processed bone marrow (in development by T2Cure, Harvest, Biomet, Thermogenesis, and others) or adipose stromal cells or adipose derived regenerative cells (Cytori Therapeutics and others) which are viewed as more variable from patient to patient.

US Patent Publ. 2010/0127342 describes how gene expression profiles from autologous cells could be developed to select patients for a given therapeutic strategy based on their likelihood of being responders to such a therapy. This is hereby included by reference, along with the references cited therein. Personalized medicine strategies for autologous tissue based therapeutics have significant potential that is not well appreciated as the diagnostic assessment of a patient's potential responsiveness can also be an analysis of the autologous dosage form's therapeutic potency.

Signature to Gate Dosage of Autologous Bone Marrow Cells for Cardiac Repair in a setting of Heart Failure of Ischemic Etiology, with or without Evidence of Active Ischemia. Delivery of autologous mononuclear cells derived from the bone marrow has been shown to be consistently safe in the setting of chronic heart failure, chronic myocardial ischemia, and acute myocardial infarction. However, while there is consensus about the safety of these cells, efficacy results from similar clinical studies in the same patient population appear to be inconsistent. Dosage is believed to be a primary culprit driving these inconsistencies. Consistent with this hypothesis, is the observation that trials with lower dosages of these cells, whether by design or due to delivery via the coronary artery route of administration have fewer positive trial results, and studies with higher cell dosages have greater rates of success. However, it is noted that higher dosage does not necessarily correlate to greater efficacy. This was observed in the Baxter study (Losordo et al. 2011) using mobilized autologous peripheral blood derived CD34+ cells in a patient population with chronic myocardial ischemia for the treatment of refractory angina whereby the smallest CD34+ cell dosage of $10^5$ cells/kg had the most significant positive efficacy results. Variations between patients in cell potency and in cell dosage delivered may also result in failed therapeutic efficacy trials.

SUMMARY OF THE INVENTION

The embodiments in this invention comprise of (1) the selection of patients for autologous tissue therapies based on the analysis of small tissue samples from the patients in advance of the therapy. Such tissues can be bone marrow, blood, tumors, muscle, heart tissue, and or other tissues known to be a viable source for autologous therapeutic cells; (2) the development of in vitro diagnostic assays in which a small amount of tissue can be assessed to see if the source tissue meets defined thresholds of cellular, protein and/or genetic characteristics that would potentially increase a patient's likelihood of being an enhanced responder to the autologous therapy.

For example, the in vitro diagnostic assay for autologous bone marrow derived mononuclear cells for the treatment of heart failure of ischemic etiology may be specified based on the CD profile of the constituent cells; (3) the development of in vitro diagnostic assays in which a small amount of tissue can be assessed to see if the source tissue meets defined thresholds of cellular, protein and/or genetic characteristics that increase a patient's likelihood of achieving a targeted therapeutic dosage when these same cells are harvested, concentrated, and re-administered at a later time point; (4) the delivery of an effective dosage based on the number of cells from a specific population, proteins and/or genes that is present in a patient that would qualify the patient as a responder to the autologous therapy; (5) the delivery of an effective therapeutic dosage based on the efficiency of the delivery route and the delivery method inclusive of the delivery system used to infuse the effective therapeutic dosage into a patient; (6) the delivery of an effective therapeutic dosage based on the patient's likelihood of having a targeted therapeutic dosage when using autologous point of care therapies that have significantly reduced costs and also enhanced safety due to the minimalist nature of the processing. Point of care systems can concentrate a particular cell population by cell density using gravity centrifugation. Many other possible means of activating cells and platelets with short term incubation with other agents, stimulating them using energy insertion such as heating or stimulating them with radiation across all the wavelengths possible or energy extraction such as cooling are possible and may be used in combination with other means of modifying tissues in a short period of time at the patient's bedside in a relatively closed system to reduce the potential contamination of the therapeutic tissues being modified. The preferred embodiment in this invention would preferably be a combination of (5) and (6) but further embodiments in this invention can also be any combination(s) of the embodiments discussed herein.

In a first aspect of the present invention, a method for screening a patient to determine a likelihood that the patient's autologous bone marrow cells (BMC) will be suitable for transplantation to a heterologous tissue site comprises providing a sample of BMC from the patient. A phenotypic profile of the BMC in the sample is obtained and assessed to determine the likelihood that the BMC will be suitable for transplantation to the heterologous tissue site without enriching particular phenotypic population(s) of the BMC beyond concentrating the cells.

The phenotypic profile is typically a CD profile, and the CD profile usually includes the concentration of cells having at least two CD markers in the sample. Often, the CD profile will include the concentration of cells having at least three CD markers in the sample. The at least two CD markers may be selected from the group consisting CD 14, CD19, CD34, CD45, CD133, and CD271 typically including at least CD34 and CD133, and often including each of CD19, CD34, and CD133. In specific examples, a sample having at least 38500CD34$^+$ cells/ml and at least 6500 CD133$^+$ cells/ml is considered suitable for heterologous transplantation for cardiac conditions in which a delivery efficiency of at least 18% as measured one hour after delivery can be achieved. In other specific examples, a sample having at least 13,000 CD19$^+$ cells/ml, at least 38,500 CD34$^+$ cells/ml, and at least 6,500 CD133$^+$ cells/ml is considered suitable for heterologous transplantation for cardiac conditions in which a delivery efficiency of at least 18% as measured one hour after delivery is achieved. The presence of CD and other cell surface markers may be conveniently assessed by comprises flow cytometry or other convention techniques.

In a second aspect of the present invention, a method for transplanting a patient's bone marrow cells to the patient comprises obtaining bone marrow cells (BMC) from the patient, where a sample of the patient's BMC has previously been tested and found to have a phenotypic profile which meets a minimum criteria for transplantation; and transplanting the BMC so obtained to a heterologous site in the patient. Any of the methods discussed above with respect to screening patient autologous BMC's may be used to identify BMC's suitable for transplantation.

The autologous BMC are typically transplanted without isolation or enrichment based on phenotype, for example without isolation or enrichment based on the presence of particular CD antigens. The autologous BMC are particularly suitable for transplanting into cardiac tissue, but can also be transplanted into other heterologous tissue sites, in including the limbs for the treatment of critical limb ischemia, as well as solid tissues, organs, membranes, blood, and the like. While the BMC will usually not be enriched or isolated with respect to their phenotype, they will often be enriched and otherwise prepared for transplantation in conventional ways without regard to phenotype. When transplanted into cardiac tissue, transplanting often comprises intra-myocardial injection, e.g. with a helical needle, and the cardiac tissue will usually be infarcted where the BMC will be able to promote regeneration of the infarcted cardiac tissue. Typically, at least 72,600 CD133$^+$ cells are present in the target heart tissue one hour after transplantation and/or at least 420,000CD34$^+$ cells are present in the infected tissue one hour after transplantation, and/or at least 144,000 CD19$^+$ cells are present in the infarcted tissue one hour after transplantation. Preferably, at least 72,600 CD133$^+$ cells, at least 162,000 CD34$^+$ cells, and at least 144,000 CD19$^+$ cells are present in the target tissue one hour after transplantation. Target tissue will typically be ischemic such as in a patient with ischemic heart failure, where injection can be into the infarct, the viable tissue, or the peri-infarct region depending on the indication.

Cells are often counted using flow cytometry relative to a standard marker on these cells such as CD45. Cells identified in the CD45/CD34/CD133 panel, CD45+/CD34+ or CD45+/CD133+ are hematopoietic stem/progenitor cells or endothelial progenitors or endothelial cells. Cells that are identified in the CD45/CD19/CD14 panel would be defined as CD45+/CD19+=B cells, CD45+/CD14+=monocytes, and cells that are identified in a CD45/CD271 panel would be defined as CD45−/CD271+ are MSCs.

In specific embodiments, a final dosage of at least 100 million BMC is transplanted to the patient.

In a third aspect of the present invention, an antibody panel comprises a first antibody or other substance which specifically binds to a first bone marrow cell (BMC) marker and a second antibody or other substance which specifically binds to a second bone marrow cell (BMC) marker. The first and second markers are characteristic of the suitability of the BMC for transplantation to a heterologous tissue site in the patient.

The at least two antibodies are specific for CD markers selected from the group consisting of CD14, CD19, CD34, CD45, CD133, CD271, with two individual antibodies typically being specific for at least CD34 and CD133, respectively, and often with three individual antibodies being specific for at least CD19, CD34, and CD 133, respectively. The antibodies in the panel may be suitable for use in flow cytometry or for any other conventional cell surface marker screening methodology.

As used herein, the phrase "bone marrow cells" (BMC) refers to the bone marrow mononuclear cell fraction.

As used herein, the phrase "autologous BMC" refers to BMC harvested from the patient to be treated with the minimally processed BMC.

As used herein, the phrase "minimally processed BMC" refers to fresh aspirated bone marrow concentrated using gravity centrifugation at the bedside. Here bone marrow mononuclear cells are concentrated by density using either a system such as the Biosafe SEPAX system, the Biomet Marrowstim System, Thermogenesis ResQ System, and the Terumo Harvest system, or the Syngen's SyngenX 2000.

As used herein, the phrase "phenotype profile," refers to gene expression profiling where RNA or protein in a sample is measured, DNA sequencing, surface marker assessment of cells such as the cluster of differentiation immunophenotyping performed on mononuclear cells, ability of the cells to meet a functional assay such as the ability to divide or proliferate, the ability to express antigens or the like in vitro, or combinations thereof.

As used herein, "CD profile" refers to the number or concentration of cells with different CD characteristics in the patient BMC. CD markers of interest include but are not limited to CD14, CD19, CD45, CD34, CD133, and CD271. In some embodiments, any one or more of the approximately 400 known CD markers may find use.

As used herein, the term "transplantation" includes all forms of tissue heterologous implantation of the BMC cells to other tissue sites. Forms of transplantation include, injection, infusion, surgical implantation, and the like. Other heterologous tissue sites include cardiac myocardium and other tissue and other tissue, such as the muscles in the legs of patients with limb ischemia.

As used herein, the term "heterologous" refers to a transplantation site in the patient other than the bone marrow that is the source of the BMC or implantation into the marrow of another bone within the body. Examples of heterologous tissue sites have been provided above.

As used herein, the term "antibodies" will refer to conventional polyclonal and monoclonal antibodies as well as recombinant antibodies, antibody fragments from any of these sources, and other specific binding substances which can specifically bind to cell surface marked with a specificity and affinity equivalent to natural antibodies.

BRIEF DESCRIPTION OF THE DRAWINGS

FIG. 2 shows calculations for estimating total doses delivered and the effective dosages of CD34$^+$, CD133$^+$ and CD19$^+$ cells.

FIGS. 4 and 5 show the minimum number of cells needed per ml of bone marrow aspirate harvested from the patient to achieve an effective dosage.

FIG. 6 shows the minimum number of cells needed per ml of bone marrow aspirate harvested from the patient to achieve an effective dosage with trans-endocardial delivery.

FIG. 8 shows the results required for a diagnostic assay output to exceed an effective therapeutic dosage form.

FIGS. 9 and 10 show a plots of the change in left ventricular ejection as a function of the CD133$^+$ and CD34$^+$ cell counts, respectively.

DETAILED DESCRIPTION OF THE INVENTION

Figure 1:
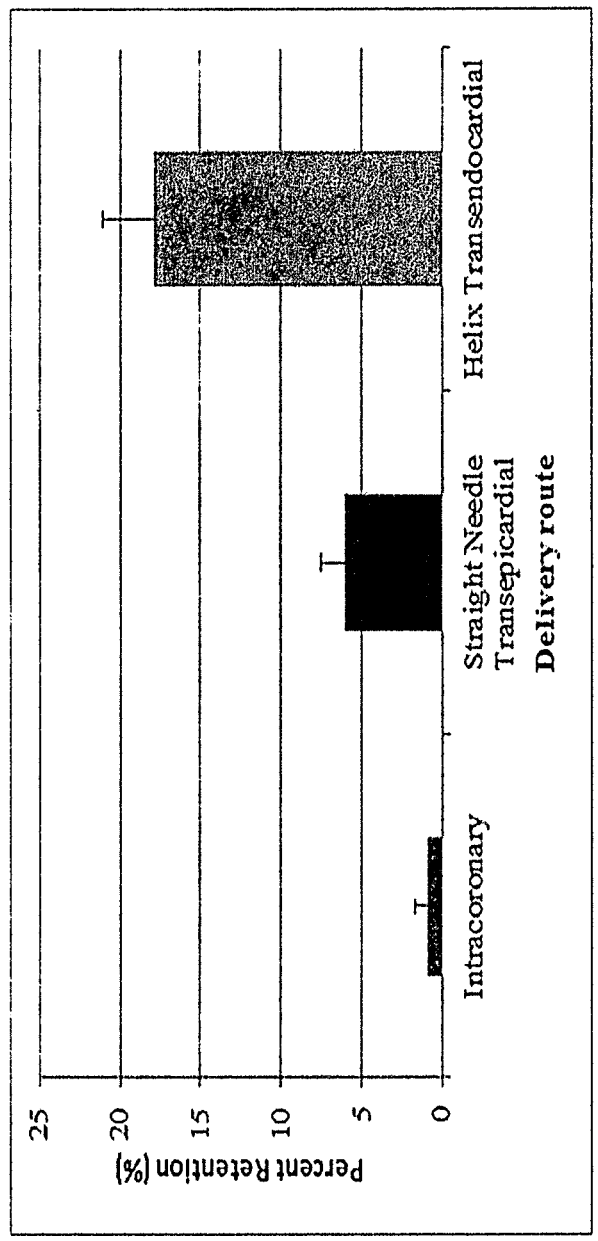
FIG. 1 is a graph comparing intracoronary artery delivery, straight needle intramyocardial delivery, and helical transendocardial intramyocardial delivery of $^{18}$F-FDG labeled bone marrow derived mononuclear cells in a swine heart.

Delivery routes and the retention of $^{18}$F-FDG labeled bone marrow derived mononuclear cells in the swine heart after 1 hour, as measured by PET-CT are summarized in FIG. 1. Intracoronary artery delivery, straight needle intramyocardial delivery, and transendocardial intramyocardial delivery of $^{18}$F-FDG labeled bone marrow derived mononuclear cells in the swine heart were compared. Here, one hour after delivery of autologous bone marrow mononuclear cells at a concentration of 100 million cells per cc, retention rates of 1% for intra coronary artery delivery, 6% for straight needle transepicardial delivery, and 18% for transendocardial delivery using the Helical Infusion catheter system were observed. For local delivery of cells, it is the local time course of regional distribution that defines the dosage and not the amount delivered. This is different for systemic delivery where dosage is often defined as the bioavailability of a therapeutic agent in the circulating blood. As many biologic agents are infused into the blood vessels, systemic dosage concentration is the same as the delivered dosage divided by the blood volume. Thus for local delivery, where agents egress from the tissue after delivery, one measure of effective dosage is the amount of agent delivered that stays at a local delivery site at a period of time after delivery. By this measure, the same number of mononuclear cells delivered transendocardially with the helix transendocardial delivery systems, straight needle intramyocardial delivery system, and intracoronary artery delivery route will result in different effective dosages due to the different retention profiles for these delivery paradigms. The phrase "effective dosage" for cell therapy is defined as the minimum dosage necessary for the cells to be retained in the tissue one hour after delivery, Patient specific cellular source material is also an issue. Patients from the FOCUS-HF Trial (Am Heart J 2011; 161:1078-1087.e3.) received 30 million autologous bone marrow cells with an intramyocardial straight needle approach, but likely had an effective dosage of 1.8 Million cells (30 million×6%) using the retention rate discussed above. The results showed that "In fresh bone marrow samples, hematopoietic and mesenchymal clonogenic assays showed decreased progenitor cell activity in our patient population." and "Autologous BMMNCs obtained from patients with stable ischemic HF have a lower hematopoietic proliferative capacity (CFU-GM) and lower migratory capacity (in response to VEGF and stromal-derived factor 1) when compared with the proliferative and migratory capacities of healthy controls." These patients did not have significant improvement in myocardial function when the overall patient population was considered. However, in a post hoc analysis, younger patients (≤60 years) who are believed to have greater potency in their cells, were observed to have significantly improved MVO$_2$.

Patients from the FOCUS-CCTRN Trial (JAMA 2012; 307(16): doi:10.1001/jama.2012.418) delivering 100 million autologous bone marrow cells using the same delivery methodology as the FOCUS-HF Trial, received an effective dosage of 6 million bone marrow mononuclear cells (100 million×6%) per the retention rate discussed above. Similarly, the FOCUS-CCTRN Trial patients did not show improvements in the primary endpoints. However, a regression analysis showed that higher CD34 cell or CD133 cell counts were associated with greater absolute unit increase in LVEF. Here, the range of CD34 was 0.5% to 6.9% (SD, 1.2%) with an average value of 2.6%. Additional analysis was claimed to suggest that every 3% higher level of CD34 cells was associated with on average a 3.0% greater absolute unit increase in LVEF in a multiple variable model that included age and treatment as predictor variables. An analogous computation for CD133 cells (range, 0.1%-3.6%; SD=0.62 with an average value of 1.2%) revealed that every 3% higher level of CD133 cells was associated with on average a 5.9% greater absolute unit increase in LVEF.

Losordo 2011, showed efficacy in a setting of refractory angina with autologous and significantly processed dosage of 1×10^5 CD34+ cells per KG (a calculated dose of 7,000,000 cells with an assumed 70 Kg average weight patient) for the clinical indication of chronic myocardial ischemia with a positive improvement in angina frequency and exercise tolerance time. This study used a straight needle intramyocardial delivery paradigm, suggesting that approximately 6% of the dosage was retained (CD34-R) in the target tissue one hour after delivery. Assuming a calculated dosage of 7,000,000 CD34 cells delivered in a 70 KG patient, the resulting effective dosage would be 420,000 CD34+ cells if the retention rate of 6% is used.

De la Fuente et al. (Transendocardial Autologous Bone Marrow in Myocardial Infarction Induced Heart Failure, Two Year Follow up in an Open Label Phase I Study, Eurointervention 2011; 7:805-812.) delivered 100 million cells using a helical needle intramyocardial approach, resulting in an effective dosage of 18 million cells at the local target sites in the peri-infarcted region of the heart. Assuming that average percent of 2.6% CD34 cells present in bone marrow mononuclear cells reported in FOCUS-CCTRN, the calculated number of CD34 cells in 18 million bone marrow mononuclear cells retained at the local target sites is 468,000 cells, which is roughly the same number of CD34+ cells as the Losordo 2011 study, shown to be therapeutically efficacious. Both the FOCUS-HF and the FOCUS-CCTRN trials had significantly lower calculated effective doses of 1.8 million and 6 million autologous bone marrow derived mononuclear cells at the local target sites of delivery.

Figure 3:
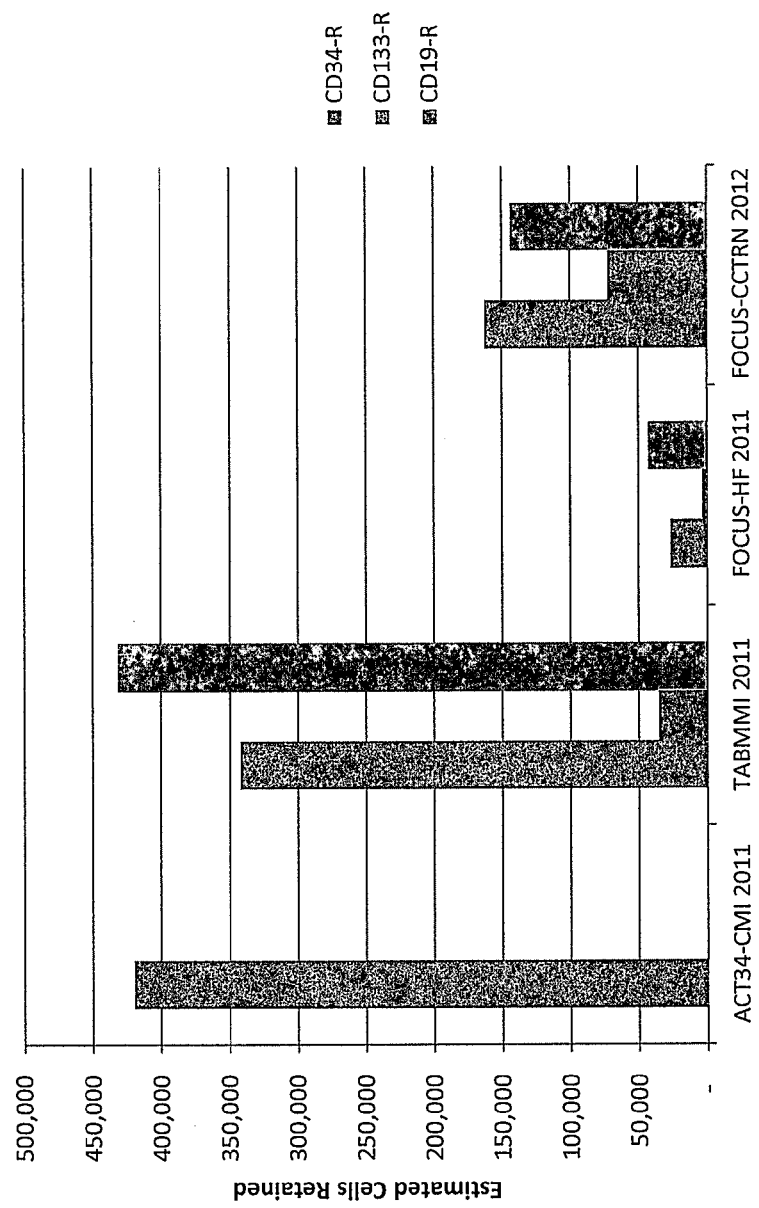
FIG. 3 shows the calculated estimated effective doses retained one hour after delivery for CD34$^+$, CD133$^+$ and CD19$^+$ cells in the four clinical trials shown in FIG. 2.

FIG. 2 shows the calculations for the estimation of the total doses delivered and the effective dosages of CD34, CD133 and CD19 cell counts retained at one hour after delivery (CD34-R, CD133-R, CD19-R) for four clinical trials (ACT34-CMI, TABMMI, FOCUS-HF and FOCUS-CCTRN) using the percent cell retention results based on the delivery routes used in the respective clinical trial as shown in FIG. 1. Here, the percentage of cells having CD34, CD133, and CD19 surface markers were all analyzed. The percent numbers in columns 3, 4 and 5 were either reported average numbers from published results for the trials or estimates taken from the closest available data. Estimates are detailed in the table with an * or a ¥. For the ACT34-CMI 2011 study, the estimate of 100% CD34+ cells was used because the CD34+ cells were first isolated from mobilized autologous peripheral blood cells and then expanded to the specific total cell dosage needed for injection. In this case, no data was shared on the purity of the formulation in question and therefore, it was assumed to be 100% purely CD34+ cells. For the TABMMI 2011 study, the percentage of CD19 cells was assumed to be the same as that in the similar patient population treated in FOCUS-HF 2011, the only clinical trial that reported on the percent of CD19 cells in the autologous bone marrow mononuclear cell fraction used in the injection procedure. Likewise for FOCUS-HF 2011, the percentage of CD133 cells was assumed to be similar to that in TABMMI 2011 as we wanted to be more conservative in our estimates. However, one could also assume that the same 1.21 percent of CD133 could be present in FOCUS-HF 2011 as was measured in FOCUS-CCTRN 2012 for a higher threshold of CD133. This would be equivalent to 363,000 CD133 cells in the autologous bone marrow mononuclear cells fraction injected in the FOCUS-HF study with an estimated 21,780 CD133 cells retained based on the straight needle intramyocardial route of delivery. FIG. 3 shows the calculated estimated effective doses retained one hour after delivery for CD34, CD133 and CD19 cells in the four clinical trials as detailed in FIG. 2.

From these results, we could consider four different scenarios as detailed in Examples 1 to 4. A simple signature that can be specified today is that any patient who has sufficient CD133 cells, and/or CD34 cells, and/or CD19 cells to achieve an efficacious therapeutic dosage form are likely to yield a far more positive response to therapy based on the best clinical data available today (Perin 2012) and any combination of one or more of these cell count thresholds can be set depending on the patient population and their level of therapeutic responsiveness.

Examples 1 to 3 below detail the development of potency assays for autologous bone marrow therapy to treat cardiac disease based on a biomarker panel which characterizes that a patient's cells will meet a threshold dose for multiple cell types that enhance potency. Effective dosage in the target delivery sites is dependent on delivery efficiency and whether the patient would have enough of these cells available in their bone marrow harvest to generate the final intended effective dosage.

EXAMPLE 1

This example describes the selection of patients for autologous tissue therapies based on the analysis of small tissue samples from the patients in advance of the therapy. Such tissue samples and patient selection is determined based on pre-defined thresholds of cellular characteristics such as number of cells per unit volume of tissue, functional capacities, gene expression profiling, and/or cell surface markers such as the levels of known cluster of differentiation (CD) surface markers of the constituent cells. The use of CD markers for immunophenotyping is well known in the art and described in commonly available resources such as: http://en.wikipedia.org/wiki/Cluster_of_differentiation. CD thresholds selected are dependent on the disease being treated and are determined based on past studies where patient improvement has been correlated with the levels of certain CD cell surface markers or other biomarkers in their tissue. In the case of heart failure patients of ischemic etiology, CD 19, CD34, and CD 133 markers are commonly looked at surface markers. In this example, potential successful patients with a higher probability of being a positive responder, can be identified as appropriate for treatment by selecting candidates with sufficient CD133, CD34, and CD19 cell counts to achieve an efficacious therapeutic dosage via their preferred delivery route. The effective dosage was calculated as the retained cells one hour after delivery in FIG. 2 and was determined to be at least 420,000 CD34+ cells (highest in Losordo 2011), 72,000 CD133 cells (highest in FOCUS-CCTRN 2012), and 144,000 CD19 cells (highest in FOCUS-CCTRN 2012; it should be noted that the percent of CD19 in the autologous bone marrow mononuclear cells used to estimate the CD19 cell count in FOCUS-CCTRN was extrapolated from FOCUS-HF) retained one hour after delivery. The assumptions used in this Example 1 lie in using the estimates of CD34 cells from the ACT34-CMI trial and in no cell losses due to cell processing. Further, assuming that a full 60 ml of bone marrow aspirate is processed from the patient, to achieve the effective dosage of at least 420,000 CD34 cells, and/or 72,000 CD133 cells and/or 144,000 CD19 cells using the Helix transendocardial delivery system, the minimum number of cells needed to be present per ml of bone marrow aspirate harvested from the patient to achieve such an effective dosage would be 38,889 CD34 cells, 6,722 CD133 cells and 13,333 CD19 cells (FIG. 4). Therefore, one could specify that a simple signature of a patient would be for him or her to have at least 38,500 CD34 cells, and/or 6,500 CD133 cells, and/or 13,000 CD19 cells per ml of bone marrow harvest. Patients who had this threshold signature in a simple small bone marrow aspirate days in advance of a procedure, are expected to have greater responsiveness to therapy. In this preferred embodiment, the patient would have 5 cc of marrow aspirated on day 1 which would have the thresholds measured using flow cytometry and reported back to the physician on day 3. Once the physician has this information, the patient could be scheduled for therapy which involves harvesting 60 ml of bone marrow from the iliac crest, concentrating it at point of care to a 5 cc volume using gravity centrifugation for delivering therapy, and delivering therapy at ten sites in 0.5 cc aliquots via transendocardial intramyocardial delivery using a catheter with a helical needle at its distal end and a means to confirm engagement with the heart using fluoroscopy. This preferred embodiment is in itself merely a broad example as other delivery systems with other efficiencies could be used to calculate different dosages. Further patients who do not meet threshold could receive a modified higher dosage so that they meet threshold.

EXAMPLE 2

Here we calculate the thresholds for a cardiac therapy as in Example 1. In Example 2, the assumptions are changed to use the effective dosage of at least 162,600 CD34 cells from the FOCUS-CCTRN clinical trial which uses autologous bone marrow mononuclear cells isolated using density gradient centrifugation with Ficoll Paque, instead of the estimated CD34 cells from the ACT34-CMI trial. The same assumption of no cell losses due to cell processing was applied. For our purpose, any reagent such as lymphocyte separating medium having the same characteristics and density as Ficoll Paque could also be used in the cell processing. Therefore, assuming that a full 60 ml of bone marrow aspirate is processed from the patient, to achieve the effective dosage of at least 162,600 CD34 cells, and/or 72,000 CD133 cells and/or 144,000 CD19 cells using the Helix transendocardial delivery system, the minimum number of cells needed to be present per ml of bone marrow aspirate harvested from the patient to achieve such an effective dosage would be 15,056 CD34 cells, 6,722 CD133 cells and 13,333 CD19 cells (FIG. 5). In this case, one could specify that a patient would qualify by having a simple signature of at least 15,000 CD34 cells, and/or 6,500 CD133 cells, and/or 13,000 CD19 cells per ml of bone marrow harvest.

EXAMPLE 3

In Example 3, instead of isolating autologous bone marrow mononuclear cells using density gradient centrifugation with Ficoll Paque or other similar reagent, we use a point of care cell processing system which concentrates autologous bone marrow or blood-derived mononuclear cells using the same technique of density gradient centrifugation without the addition of Ficoll Paque. In this case, we further assume 20 to 50 percent cell losses due to the cell processing. Therefore, assuming that 54 ml of bone marrow aspirate is processed from the patient (it should be noted that 54 ml of bone marrow aspirate is used here to take into account the 6 ml of heparin or other anticoagulating agent used to typically make up the full volume of 60 ml during bone marrow harvest), to achieve the same effective dosage of at least 162,600 CD34 cells from the FOCUS-CCTRN clinical trial, and/or 72,600 CD133 cells, and/or 144,000 CD19 cells using the Helix transendocardial delivery system, the minimum number of cells needed to be present per ml of bone marrow aspirate harvested from the patient to achieve such an effective dosage would be 20,910 to 33,457 CD34 cells, and/or 9,336 to 14,938 CD133 cells, and/or 18,519 to 29,630 CD19 cells (FIG. 6). In this case, if we want to be conservative, we could specify that a patient would need to have a simple signature of at least 33,500 CD34 cells, and/or 15,000 CD133 cells, and/or 30,000 CD19 cells per ml of bone marrow harvest. On the other hand, we could assume that the point of care cell processing system is a lot more efficient and that 80% of the cells processed are typically recovered from the system such that a patient would need to have at least 21,000 CD34 cells, and/or 9,500 CD133 cells, and/or 19,000 CD19 cells per ml of bone marrow harvest. Any combination of number of CD34 cells, CD133 cells and CD 19 cells within the 50 to 80% recovery range could potentially be used to pre-specify thresholds for a patient based on the known efficiency of the system used. This efficiency of cell recovery rate could already be known or could be determined or changed prospectively after the processing of a number of samples.

EXAMPLE 4

Figure 7:
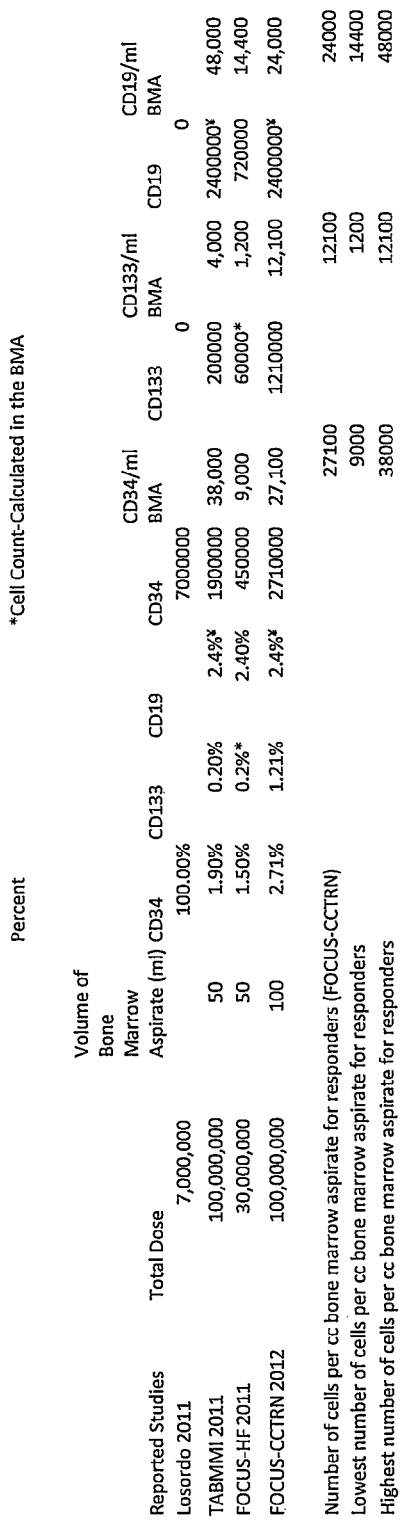
FIG. 7 shows a partial response of a patient population.

An embodiment of this invention whereby we consider that the patient would potentially be responsive to a therapy that may or may not be autologous merely based on the levels of certain CD markers in their bone marrow aspirate. Bone marrow cells respond to therapies that stimulate the expression of chemokines in tissues. For cardiac applications, allogeneic mesenchymal stem cells, allogenic mesenchymal precursor cells, and allogeneic cardiosphere derived cells are all in clinical development and reportedly act by a mechanism of action in which paracrine signaling triggers a response in the patient. These responses very likely involve the cells of the immune system and developing a responsiveness assay has significant value for these patients. This is more in line with the classic strategy of pharmacogenomics, but here we are looking specifically at the responsiveness of the gene expression, surface markers, or cell counts of cells from the bone marrow. This strategy may be used similarly with autologous therapies that are either highly processed or minimally processed. Looking at the FOCUS-CCTRN trial only as an example of a patient population that almost responded, the potential responders would have to have at least 27,100 CD34 cells, and/or 12,100 CD133 cells, and/or 24,000 CD19 cells per cc of bone marrow aspirate (FIG. 7). This is the half of the population with the most potent cells.

EXAMPLE 5

A therapy of 200 Million Autologous Bone Marrow Mononuclear Cells Concentrated using Gravity Centrifugation with the Cells from 60 cc of bone marrow aspirate is to be developed. The results required for the diagnostic assay output to exceed an effective therapeutic dosage form with at least 420,000 CD34 cells, 144,000 CD19 cells, and 72,600 CD133 cells remaining in place sixty minutes after delivery are shown in FIG. 8 for both a 1 cc and a 10 cc aspirate. If the efficiency of delivery was 100%, most patients would likely qualify. The number of patients that qualify decrease significantly as the efficiency of delivery decreases. This erodes the value of the therapy. FIG. 8 shows the cell counts that must be present to achieve the therapeutic dosage with the perfect 100% retention in the tissue one hour after delivery, as well as with the percent retention achieved with three leading delivery systems: transendocardial delivery with the helical infusion system (BioCardia, Inc. San Carlos, Calif.), a straight needle system such as transepicardial syringe delivery system, and an intracoronary artery infusion system using a standard balloon catheter. Other delivery systems and methods used to achieve different retention results one hour after delivery can be within the scope of this invention. For example if extreme care is used and a transepicardial needle is inserted at a significant angle, cell retention in the tissue can be greater. Many other variables which affect retention including timing of delivery with respect to the heart cycle, volume of delivery, target tissue for delivery etc., can be modified.

A preferred embodiment here is the use of a diagnostic assay to select patients who have at least 21,000 CD34$^+$ cells, 9,500 CD133 $^+$cells, and 19,000 CD19$^+$ cells per cc bone marrow aspirate from their iliac crest to receive the delivery of one to ten cc of cells concentrated from a fifty-four (54) cc. harvest of bone marrow aspirate by a point of care cell concentration system The cells are then delivered to up to fifteen locations adjacent to damaged tissue using the Helix Infusion System. It is noted that immature CD19 cells also express CD34$^+$ cells (Loken M R et al, Flow Cytomeric Analysis of Human Bone Marrow II. Normal B Lymphocyte Development, Blood Vol 70, No 5; 1987 pp1316-1324.). Patients who fail to meet this threshold may not be selected for treatment.

Clearly, these threshold values can be calculated based on the efficiency of delivery of any delivery platform. For less efficient delivery systems than the Helix transendocardial delivery system, such as the straight needle endocardial or straight needle epicardial systems, an operator could pull more marrow for processing to meet the relative threshold for effective dosages of these cell types. However, as the volume extracted increases, the pain and discomfort to the patient increases. Further, thresholds of one or more cell surface markers may be selected for this and other types of therapies.

The processing platform efficiency must also be considered. With the Helix Transendocardial Delivery System and the Marrow Stim processing platform for processing 60 cc of marrow, a final volume of 6 cc concentrate can be obtained. If only 5 cc of marrow at a concentration of 40 million cells per cc is to be used for therapeutic purposes, the aspirate thresholds would be higher as a portion of the cells (1 cc) will not be delivered. The thresholds are easily calculated as has been described.

As one treats and follows many patients tracking details on the cell characteristics will help to enhance understanding of threshold levels and new thresholds may be set. Such in vitro multivariate analyte assay can be run as a homebrew assay in a Clinical Laboratory Institute of America without FDA clearance or can be submitted for a deNovo 510(k) pathway for FDA approval.

Other trial result thresholds may be set. FIG. 9 shows a plot of the change in left ventricular ejection as a function of the CD133 cell counts delivered from action from the TABMMI trial. There is a clear trend in the patients with higher CD133 cells in that they have more improvement and this is in agreement with the post hoc analysis reported in the literature in FOCUS-CCTRN 2012. Here the threshold of 30,000 cells delivered with Helix is set in which all patients above this threshold are responders. This is shown by line 501. This is the threshold set based on delivery with the Helical Infusion Catheter and with a 18% retention corresponds to a 7500 CD133 cell effective dosage in autologous concentrated bone marrow mononuclear cells. This can be used to define the thresholds that must be present in aliquots taken from the patient before therapy as shown in FIG. 8.

It should be clear that additional data which already exists but which has not been published could be used to define a new threshold, and that a threshold could be set where 100%, 90%, 80%, or even only 70% of the patients respond based on other parameters. Further, merely running larger trials and tracking cell phenotype and response to therapy will enable these thresholds to be revised and validated in subsequent prospective clinical trials if needed. Further, as noted, increasing the dosage or modifying delivery to enhance retention and therapeutic dosage can enable modifications in a therapeutic strategy to enable more patients to have potential to receive therapeutic benefit. In this way, one may tailor the therapy to a specific group of patients or even a particular patient in a personalized medicine approach so that the patients would receive optimal therapeutic benefit.

Based on the patients treated in FIG. 4, at 100M cells with helix this threshold criteria excludes more patients from therapy than a 200M cells with helix using this same threshold criteria.

As similarly shown in FIG. 10, using the dosage of Losordo to set a threshold of 420,000 for effective dosage of $CD34^+$ cells with Helix in TABMMI 2011 would correspond to 420,000 divided by the efficiency of delivery of 0.18 results in the need to deliver 2,333,333 CD34+ cells. This would exclude 13 of 17 patients at dosage of 100M cells with helix as assessed from the results with the TABMMI trial shown as line 701. However at a dosage of 200M cells delivered using the same patients with helix the threshold line would move to the left 702 and all but three patients would meet the threshold. Here we assume that there are no synergistic or antagonistic effects of other cells in the autologous bone marrow concentrate, which will either be validated or challenged by data obtained in clinical trials.

Here a simple 50 ml aspirate and point of care processing at a cost of a few hundred dollars has potential to replace a $CD34^+$ therapy obtained by GCSF stimulated release of the cells from the bone marrow, apheresis of the patient's blood to extract the cells, and isolation of only the cells of interest at a cost of $10,000 to $25,000. If there are synergistic effects of the other cells it may also prove to be a better therapy. If antagonistic, additional data may be used to predetermine thresholds and dosages to deliver an effective dosage of autologous minimally processed cells.

Of note, although the patients in TABMMI 2011, FOCUS 2011, and FOCUS 2012 were of similar phenotypes, the first had no active ischemia and the latter two had mostly active ischemia (FOCUS 2012 was changed to allow non-ischemic patients into the trial midway through). The CD $34^+$ cells available in the bone marrow of these different patient populations varied greatly. $CD34^+$ cell counts per cc of bone marrow aspirate in FOCUS-CCTRN 2012 exceeded that in TABMMI 2011 and FOCUS-HF 2011. Clearly, precision in establishing measurement techniques for setting these thresholds will be important in larger trials and future development. Understanding that cells are counted the same way in a series of trials and knowing both average and standard deviations for threshold setting will be important.

CD19 expressing cells have also been detailed as important potential therapeutic agents. Here, therapeutic threshold is set at the reported median average for these cells in the tissue of patients with heart failure as reported in FOCUS-HF 2011 (a negative trial) with the three fold increase in dosage and threefold increase in efficiency of delivery as reported by the inventors in TABMMI 2011. This effective dosage value would be 600,000 cells. The selection of this threshold is expected to eliminate half of the patients at 100M cells used in TABMMI, but a much smaller number of patients at a dosage of 200M cells.

A patient can be selected for a predefined dosage form by assessing the suitability of their autologous tissues to meet predefined effective dosages that can be achieved using available delivery systems. Suitability can be assessed using cell surface markers as detailed here, using gene expression analysis as detailed in 2010/0127342, combining these techniques, incorporating other molecular measurement techniques, such as the ease with which they express a particular surface antigen, and even incorporating details of the phenotypic characteristics of a patient and their disease state. For example, the thresholds for one or more CD cell surface markers in combination with one or more gene expression values for one or more patient phenotypic characteristics is likely to evolve over time. Such clinical phenotypic criteria that includes race, sex, age, diet, and other risk factors may be incorporated in such an analysis as independent variables. The elegance of this method of developing thresholds of efficacy for autologous cell based therapies is that autologous therapies can evolve over time as we learn more of the potential of these cells to treat known and unknown diseases.

A therapeutic dosage form may also be set by one or multiple of these CD cell surface markers, other cell surface antigens, proteins and/or genes, as well as functional assays. Selecting patients for therapy and setting their required dosages to be delivered via specific delivery systems and delivery routes based on what appears to be retained for effective local dosage one hour after delivery depending on their available autologous tissue and available delivery technology is a novel therapeutic approach and will result in far less expensive and more effective products for the treatment of patients.

The methods for analyzing multiple variables include principal components analysis, linear discriminant analysis (LDA, StatSoft, Inc.), logistic regression (SAS Institute, Inc.), prediction analysis of microarrays (PAM) voting, classification and regression trees (TreeNet, Salford Systems), Random Forests, nearest shrunken centroids and k-nearest neighbors.

Once a small set of variables (cell surface markers, gene expression thresholds, protein expression levels, and/or phenotyping patient information) are selected, confirming their potential to act as a signature for therapeutic efficacy may require tuning and will require clinical validation. Tuning involves defining an equation with the variables to optimally separate the responders from the non-responders and testing involved validation of the test results in a clinical study. Some groups (Deng et al American Journal of Transplantation 2006; 6: 150-160) have used these techniques to develop a linear discriminant analysis system which is relatively simple, other approaches are also possible which do not reduce the output to a simple scalar score.

One approach involves ranking the variables for their ability to independently separate the groups (responders versus non-responders) and constructing a tree shaped map that ranks the variables based on their ability to separate the responders from the non-responders. Each variable creates three scenarios: (A) a probability greater than 50+X% that patient is a responder, (B) a probability greater than 50+X% that patient is a non-responder, or AB indeterminate in which neither A nor B is true. X may be selected and need not be that large for this technique to work well. The first variable that separates with the greatest degree of confidence for a given X then defines three classes: A1, B1, and AB1. This is the trunk of the graphical tree. The second variables build on this scoring and one gets nine separate classifications possible: A1A2, A1B2, A1AB2, B1A2, B1B2, B1AB2, AB1A2, AB1B2, AB1AB2. This is the first set of branches off of the trunk branches. A third variable similarly results in 81 independent states that may be assessed and so on. This is the third set of branches. Such a graphical readout is possible for tens of variables which with color coding of the As and Bs one can begin to readily interpret patterns where there is high confidence on therapeutic effectiveness without discarding important data that may be useful for future analysis and interpreted graphically for up to 20 ranked variables (including quality control genes such as plant genes, or surface markers that appear on all cells). If X is selected to be vanishingly small, a binary score is possible that makes tracking the decision aspects of each variable contributor to the algorithm much simpler. As yet undefined algorithms may be employed in this invention as there is significant ongoing work in this area.

For bone marrow cells to treat ischemic heart failure, the thresholds disclosed here can be validated by use of these thresholds as inclusion criteria for clinical trial design. A clinical trial that achieves therapeutic efficacy based on the use of these criteria, would be considered validation of the criteria. Over time the criteria may be modified in further investigational clinical studies. For example, if a successful validation suggests that a large portion of patients are being excluded from therapy because they typically don't have one variable's threshold met, a clinical non-inferiority study could be run to assess the ability to lower the threshold of one or more variables. Similarly, if there is a new variable that is believed to enhance therapeutic potential, trials could be performed to assess patient benefit based on a modified threshold including that new variable, without invalidating the previous thresholds set. This includes all the characterized CD molecules generated by studies of leukocyte surface molecules, organized through a series of international workshops known as the Human Leucocyte Differentiation Antigens (HLDA) Workshops. A full list of current characterized CD molecules is available on the Human Cell Differentiation Molecules (HCDM) website (http://www.hcdm.org), an organization that runs the HLDA Workshops and names and characterizes CD molecules (http://www.uniprot.org/docs/cdlist). These CD molecules are a major focus and are widely used in research where their up regulation or down regulation have been found to play a significant role in differential diagnosis, monitoring and treatment of many diseases. At present, CD markers CD1 to CD364 are current.

The detailed description of thresholds for this invention focus on ischemic heart failure patients and autologous bone marrow mononuclear cells. However, other autologous cell types for a variety of indications could benefit from this therapeutic strategy—both for initial product approvals and improvement in efficacy over time. This includes adipose-derived regenerative cells (Cytori), expanded CD34+ cells (Cell ProThera), cord blood cells (Perkin Elmer), expanded autologous multicellular therapy including primarily autologous mesenchymal stem cells (Aastrom Biosciences Inc.), expanded autologous bone marrow-derived mesenchymal cardiopoietic cells (Cardio3 Biosciences), and CD34+, CD133+, and CD19+ enriched bone marrow or blood-derived progenitor cells (Baxter, Miltenyi, and AC Therapeutics) for the indications of cardiovascular disease (ischemic heart failure, non-ischemic heart failure, diastolic heart failure, systolic heart failure, chronic myocardial ischemia and ischemic heart failure without active ischemia or chronic myocardial infarction), autoimmune diseases such as Lupus, inflammatory bowel diseases such as Crohn's and ulcerative colitis, diabetes, and renal diseases, as well as immunological strategy for treating cancer with harvested and re-administered autologous immune cells. For cord blood cells, taken at birth, the diagnostic element towards efficacy would be performed on cells from the banked cell samples intended for therapy. This could be done with other cell types as well.

All patents, publications, and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

While the above is a complete description of the preferred embodiments of the invention, various alternatives, modifications, and equivalents may be used. Therefore, the above description should not be taken as limiting the scope of the invention, which is defined by the appended claims.

What is claimed is:

1. A method for screening a patient with chronic myocardial ischemia or heart failure of ischemic etiology to determine a likelihood that the patient's autologous bone marrow cells will be suitable for transplantation to a heterologous tissue site to treat the patient's chronic myocardial ischemia or heart failure of ischemic etiology, said method comprising:

providing a sample of bone marrow cells (BMC) from the patient with chronic myocardial ischemia or heart failure of ischemic etiology;

obtaining, with a cell counter, a phenotypic profile of the BMC in the sample, wherein the phenotypic profile comprises a CD profile comprising the concentrations of $CD19^+$, $CD34^+$, and $CD133^+$ cells; and determining, with the cell counter, whether individual concentrations of CD19+, CD34+, and CD133+ cells in the CD profile each meet or exceed threshold concentrations of $CD19^+$, $CD34^+$, and $CD133^+$ cells, respectively, to identify the BMC from the patient with chronic myocardial ischemia or heart failure of ischemic etiology as being suitable for transplantation to the heterologous tissue site without enriching particular phenotypic population(s) of the BMC to treat the patient's chronic myocardial ischemia or heart failure of ischemic etiology, wherein the BMC from the patient with chronic myocardial ischemia or heart failure of ischemic etiology are identified as suitable for said transplantation if each of the determined individual concentrations of CD19+, CD34+, and CD133+ cells meet or exceed the threshold concentrations of CD19+, CD34+, and CD133+ cells, respectively.

2. A method as in claim 1, wherein the CD profile consists solely of $CD19^+$, $CD34^+$, and $CD133^+$ cells.

3. A method as in claim 1, wherein the concentrations comprise threshold concentrations of 21,000 $CD34^+$ cells, 9,500 $CD133^+$ cells, and 19,000 $CD19^+$ cells.

4. A method as in claim 3, wherein the concentrations comprise threshold concentrations, at least 27,100 $CD34^+$ cells/ml, 12,100 $CD133^+$ cells/ml, and 24,000 $CD19^+$ cells/ml.

5. A method as in claim 1, wherein the sample of bone marrow cells (BMC) comprises bone marrow aspirate.

6. A method as in claim 5, wherein the bone marrow aspirate is treated only with an anticoagulant.

7. A method as in claim 1, wherein the cell counter comprises a flow cytometer.

\* \* \* \* \*